United States Patent [19]
McDonald

[11] Patent Number: 5,578,080
[45] Date of Patent: Nov. 26, 1996

[54] PLASTIC OPTICAL LENS WITH REDUCED THICKNESS LIGHT BLOCKING SEGMENTS, AND ANCHORING MEANS

[75] Inventor: Henry H. McDonald, 800 E. Colorado Blvd., Suite 450, Pasadena, Calif. 91101

[73] Assignees: Henry H. McDonald; William W. Haefliger, both of Pasadena, Calif.

[21] Appl. No.: 423,216

[22] Filed: Apr. 17, 1995

Related U.S. Application Data

[63] Continuation of Ser. No. 103,573, Aug. 9, 1993, abandoned, which is a continuation-in-part of Ser. No. 43,009, Apr. 5, 1993, Pat. No. 5,425,759, which is a continuation of Ser. No. 807,204, Dec. 16, 1991, Pat. No. 5,203,790, which is a continuation-in-part of Ser. No. 791,002, Nov. 12, 1991, Pat. No. 5,203,789.

[51] Int. Cl.⁶ .................................................. A61F 2/16
[52] U.S. Cl. .................................................. 623/6
[58] Field of Search .................................................. 623/6

[56] References Cited

U.S. PATENT DOCUMENTS

| 4,441,217 | 4/1984 | Cozean, Jr. | 623/6 |
| 4,573,998 | 3/1986 | Mazzocco . | |
| 4,605,409 | 8/1986 | Kelman | 623/6 |
| 4,731,078 | 3/1988 | Stoy et al. . | |
| 4,769,035 | 9/1988 | Kelman | 623/6 |
| 4,786,445 | 11/1988 | Portnoy et al. . | |
| 4,790,846 | 12/1988 | Christ et al. . | |
| 4,813,957 | 3/1989 | McDonald . | |
| 4,833,890 | 5/1989 | Kelman | 623/6 |
| 4,834,751 | 5/1989 | Knight et al. . | |
| 4,840,627 | 6/1989 | Blumenthal | 623/6 |
| 4,842,602 | 6/1989 | Nguyen . | |
| 4,880,013 | 12/1989 | Ting et al. . | |
| 4,880,426 | 11/1989 | Ting et al. . | |
| 4,888,014 | 11/1989 | Nguyen . | |
| 4,894,062 | 1/1990 | Knight et al. . | |
| 4,932,970 | 6/1990 | Portney . | |
| 4,938,767 | 7/1990 | Ting et al. . | |
| 4,957,505 | 9/1990 | McDonald . | |
| 4,959,070 | 9/1990 | McDonald . | |
| 4,978,354 | 12/1990 | Van Gent | 623/6 |
| 5,030,231 | 7/1991 | Portney . | |
| 5,044,743 | 9/1991 | Ting . | |
| 5,203,789 | 4/1993 | McDonald | 623/6 |
| 5,203,790 | 4/1993 | McDonald | 623/6 |
| 5,217,464 | 6/1993 | McDonald | 623/6 |
| 5,425,759 | 6/1995 | McDonald | 623/6 |

Primary Examiner—Randy C. Shay
Attorney, Agent, or Firm—William W. Haefliger

[57] ABSTRACT

A plastic lens insertible into the eye lens zone from a natural lens has been removed, the plastic lens having a light passing intermediate and bead-like optical portion; the lens also having a peripheral portion or portions bounding the intermediate portion and characterized as subtsantially light blocking.

11 Claims, 8 Drawing Sheets

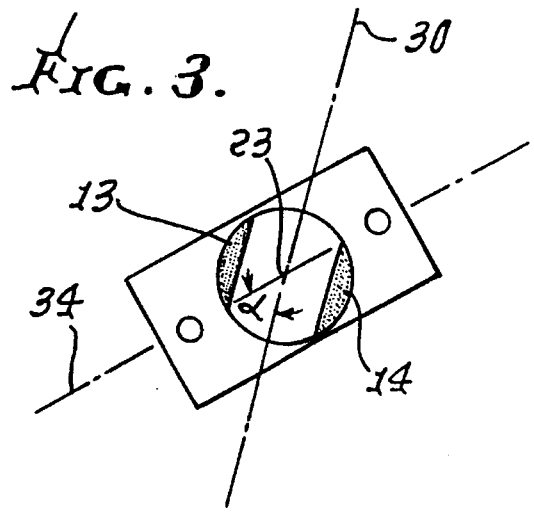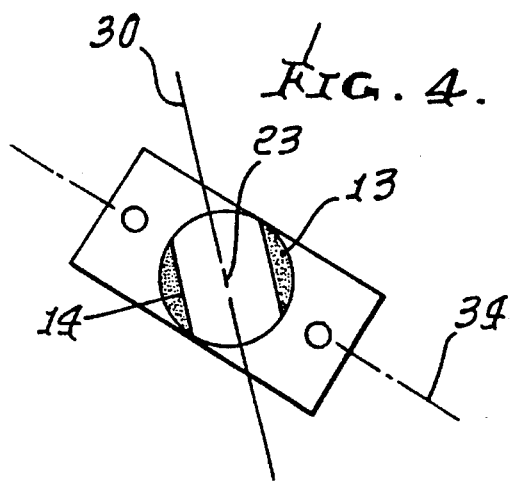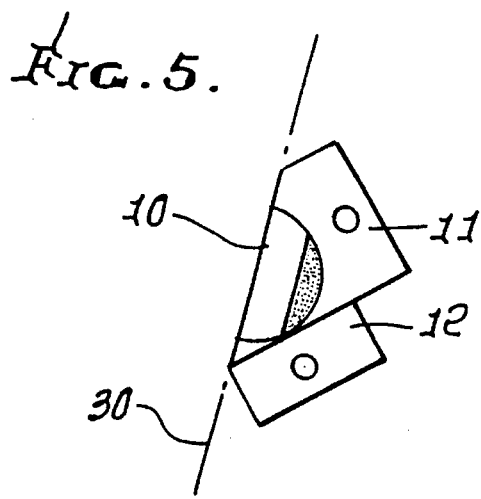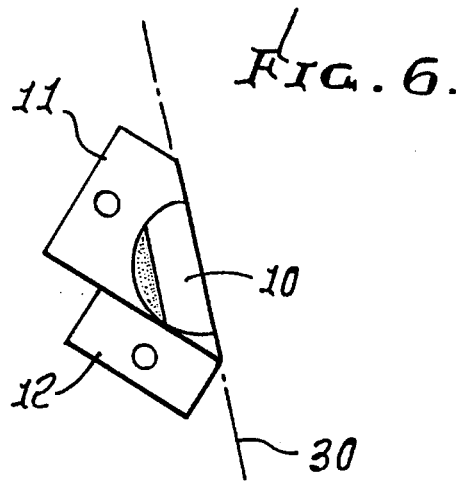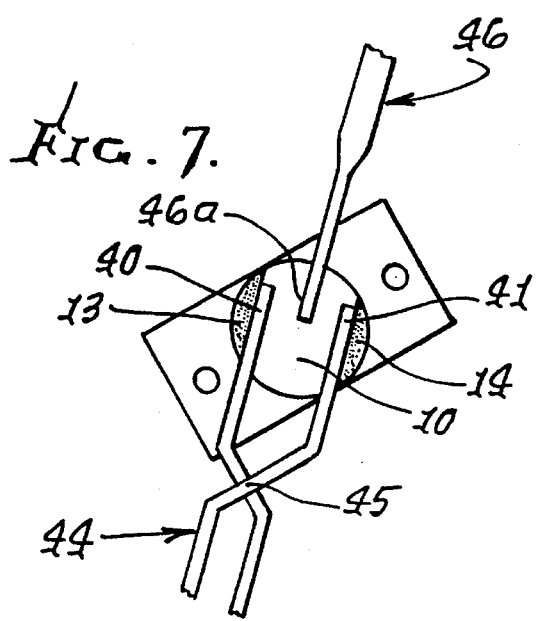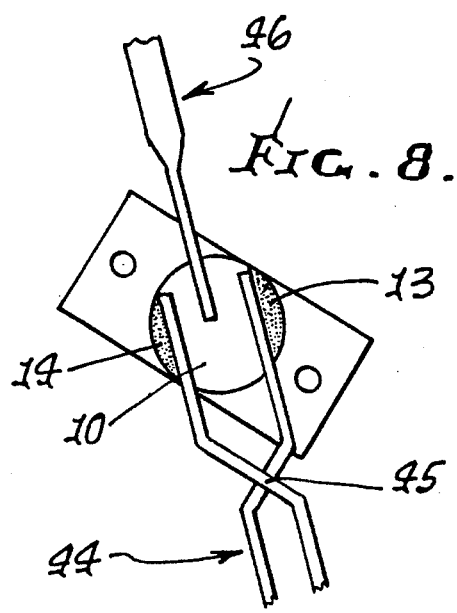

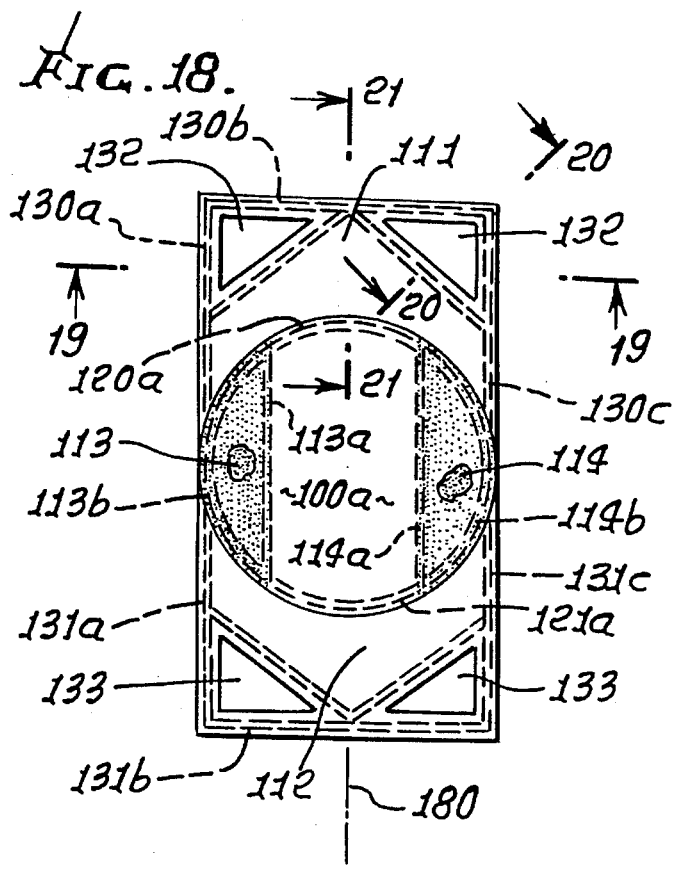
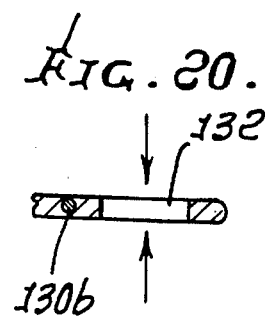
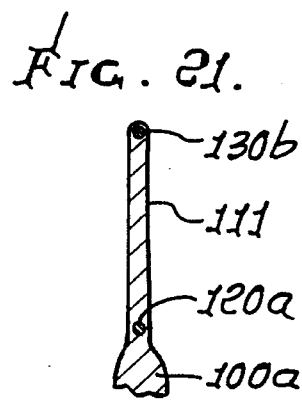
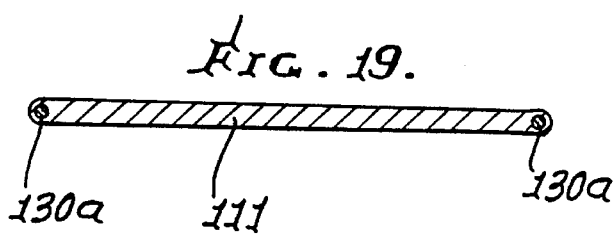
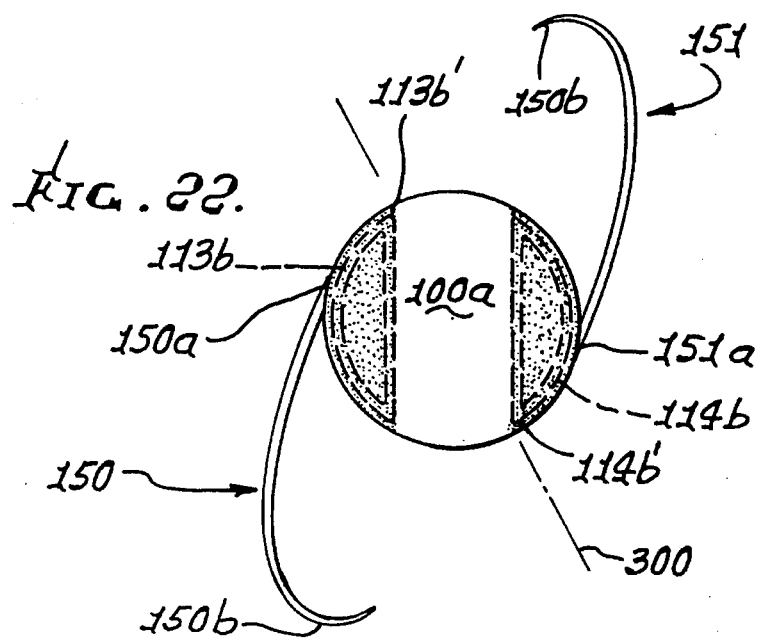

PLASTIC OPTICAL LENS WITH REDUCED THICKNESS LIGHT BLOCKING SEGMENTS, AND ANCHORING MEANS

This application is a continuation of application Ser. No. 08/103,573 filed Aug. 9, 1993, now abandoned, which is a continuation-in-part of Ser. No. 08/043,009 filed Apr. 5, 1993, now U.S. Pat. No. 5,425,759 which is a continuation of Ser. No. 807,204 filed Dec. 16, 1991, now U.S. Pat. No. 5,203,790, which is a continuation-in-part of Ser. No. 791,002 filed Nov. 12, 1991, now U.S. Pat. No. 5,203,789.

BACKGROUND OF THE INVENTION

This invention relates generally to method and apparatus for insertion of a lens or optic through a narrow width incision in the eye; and into the corneo-scleral limbus of the eye; and more particularly concerns formation and use of a lens having light occluding, de-bulked portions or segments to facilitate such insertion.

Recent efforts to achieve clear vision by use of a lens implant have led to use of a hard, plastic lens of narrowed width to be passed through an incision or wound (of about 7 mm length) in the eye surface. However, visual distortion can then result, because external light rays can then pass through the pupil extents not covered by the reduced dimension lens implant, during decentering of the lens implant in the eye, or enlargement of the pupil.

Visual distortion and "glare" become increasingly disabling with either enlargement of the pupil, or decentration of the lens implant, both of these being possible under extreme conditions. Decentration occurs when the lens implant is improperly placed in the eye, or adhesions draw the implant out of centered condition. Further, the pupil can be dilated excessively due to medication or stimulation such as created by fear or excitement, or in a dark environment.

There is, accordingly, need for a means to alleviate the problem of such visual distortion, as well as need for improvements in soft lenses that will avoid the visual distortion problem, as well as aid insertion of such lenses, including extra large and bulky lens masses of larger diameters as through narrowed incisions.

There is also need for a distortion-alleviating provision of an opaque zone of the lens, especially when de-bulking of the optic is present, and especially under decentration conditions.

SUMMARY OF THE INVENTION

It is a major object of the invention to provide a special lens implant which overcomes the above problems in a very simple manner. The invention in part contemplates use of a soft lens having abruptly reduced bulk and thickness, at an opaque edge segment or segments, which may complete the lens fold cross-dimension (typically about 3 mm to 6 mm).

Basically, the malleable lens (for example consisting of silicon) of the present invention incorporates at least one de-bulked or thinned peripheral segment and preferably two peripheral segments, such segments also characterized as occluded or darkened to prevent light ray passage. Such segments are positioned at locations such that the light-passing extent of the lens has reduced width (as referred to above) between the segments, but can have normal width along an axis parallel to the segments, and the lens may be foldable to pass through the narrow width incision in the eye, or may remain unfolded. The reduced thickness segments typically also form pockets to receive and locate the forceps blades during lens folding, and implantation, in the eye, for better and more reliable control of these steps, as will be seen.

It is another object of the invention to provide an implantable lens that facilitates insertion through an incision in the eye, and which also enables reduction in lens size, through use of occluded lens segments, de-bulked in size. Basically, the lens of the invention is characterized as a) having a light passing intermediate and bead-like optical portion, and two oppositely extending haptics, b) the lens also having two opposed peripheral segments characterized as light blocking, c) the segments having substantially reduced thickness relative to the thickness or thicknesses of the main extent of the intermediate optical portion.

As will be seen, the two segments are typically of substantially equal size and shape, and may extend adjacent the intermediate optical portion along a substantially linear border. Further, the lens has an optical axis, and there being a flat plane containing the optical axis which bisects one of the segments and also bisects the other of the segments.

It is another object to provide a lens as referred to wherein the haptics are in the form of flat and flexible plastic tabs that extend directionally longitudinally oppositely, the segments each elongated in skewed relation to the haptics longitudinal direction. The lens may be foldable along a fold axis parallel to the two segments, to bring the flexible segments into superposition for insertion through a very small width eye incision, and into the corneo-scleral limbus. The two segments may abruptly taper away from the intermediate optical portion of the lens, and the lens may be gripped by forceps at the superposed reduced thickness segments to enhance grippability of the folded lens, as during its insertion into the eye along with haptics attached to the lens, to ensure gripping of the lens during its controlled rotary positioning in the eye, and to enable controlled release and expansion of a folded lens, i.e., prevent "explosive expansion".

It is another object of the invention to provide an implantable lens with a light passing intermediate optical portion, the lens also having peripheral portions or structure bounding the intermediate portion and characterized as substantially light blocking, such as occluding. Such a plastic lens may have an overall cross dimension of about 8 mm–10 mm and may be implantable following provision of a correspondingly sized incision in the eye. In this regard, the peripheral portions or structure may be de-bulked in size, i.e., have reduced thickness relative to the thickness of the lens intermediate portion, which is light passing.

It is another object of the invention to provide haptic means extending integrally with the bounding peripheral portion or portions, such haptic means being tabular or filament-like in structure, for example, and as will be described. Such a lens may be inserted into the eye in an unfolded or folded condition.

The method of the invention typically includes the steps:

i) forming a light passing intermediate and bead-like intermediate optical portion, ii) and molding a peripheral portion or portions integral with and bounding the intermediate portion and characterized as substantially light blocking.

These and other objects and advantages of the invention, as well as the details of an illustrative embodiment, will be more fully understood from the following specification and drawings, in which:

DRAWING DESCRIPTION

FIG. 3 is a front view of a lens as in FIG. 1, together with attached solid haptics;

FIG. 4 is a rear view of the FIG. 3 lens and haptics;

FIG. 5 is a front view of the FIG. 3 lens and haptics in folded condition;

FIG. 6 is a rear view of the FIG. 5 folded lens and haptics;

FIG. 7 is a front view showing use of holding and folding forceps during lens folding;

FIG. 8 is a rear view of the FIG. 7 forceps and lens during folding;

Figure 1:
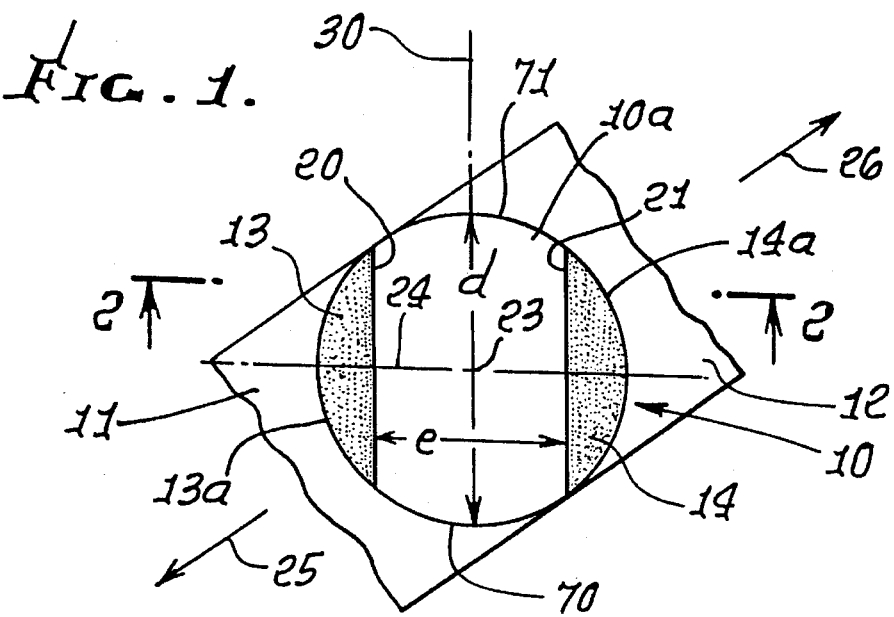
FIG. 1 is a front view of a modified plastic lens incorporating the invention.
Figure 13:
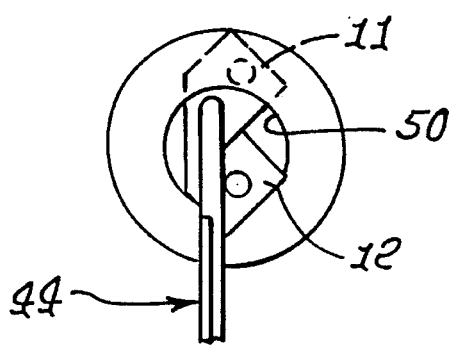
Figure 14:
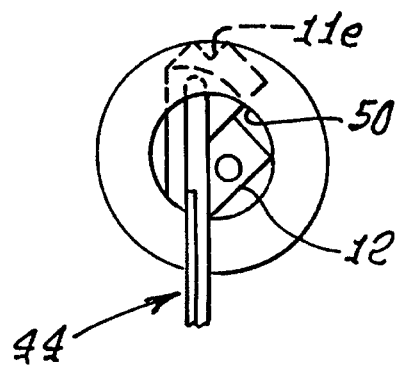
Figure 9A:
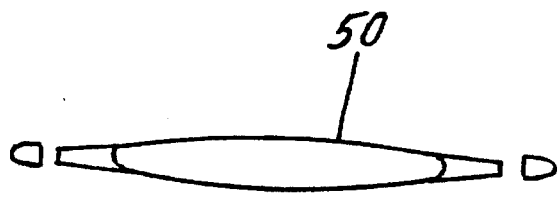
Figure 9B:
Figure 9C:
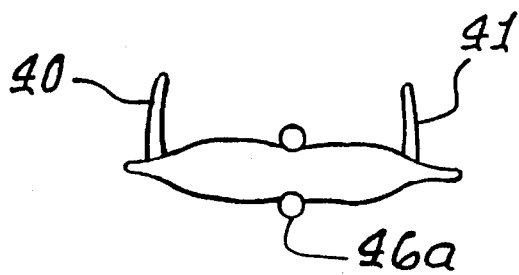
Figure 9D:
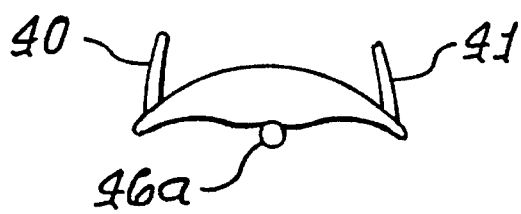
Figure 9E:
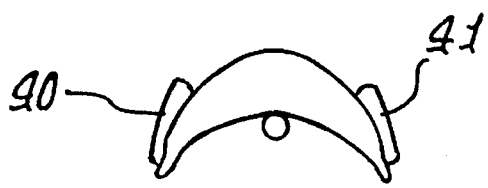
Figure 9:
Figure 9G:
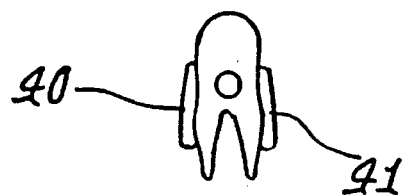
Figure 11:
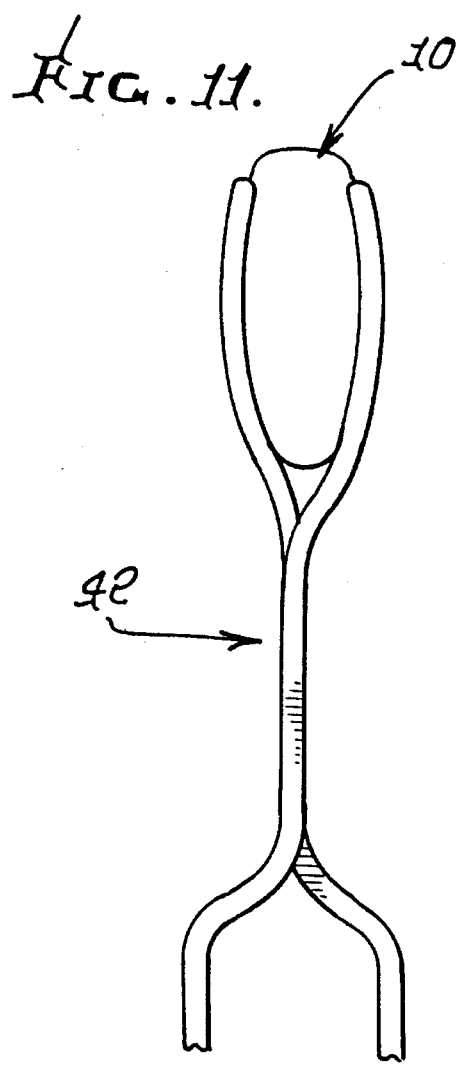
Figure 12:
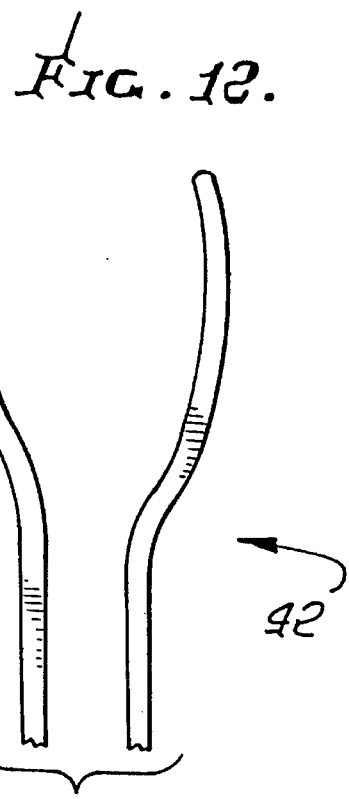
Figure 15:
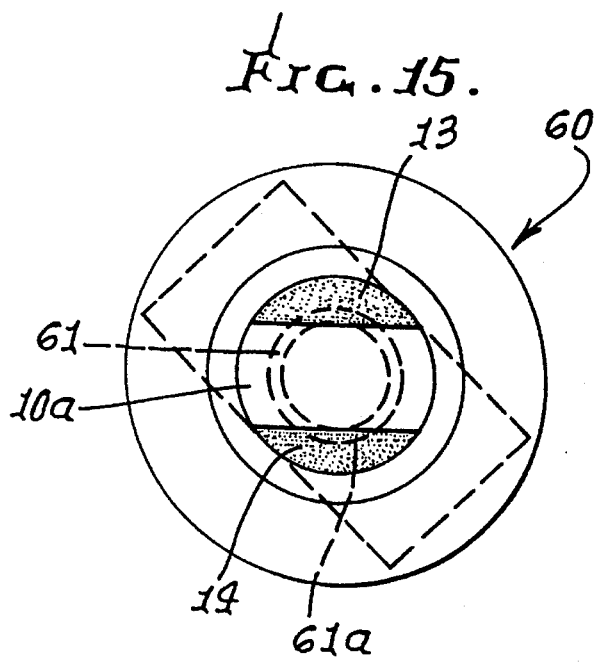
Figure 10:
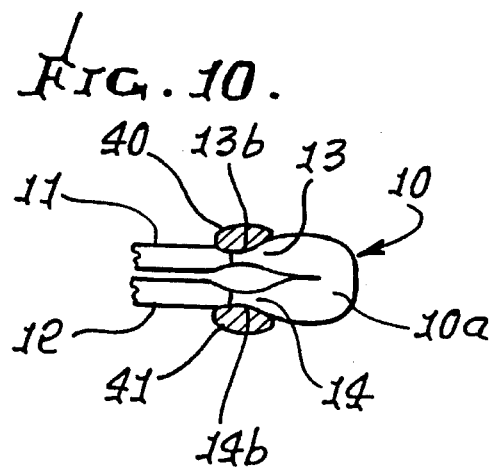
Figure 16:
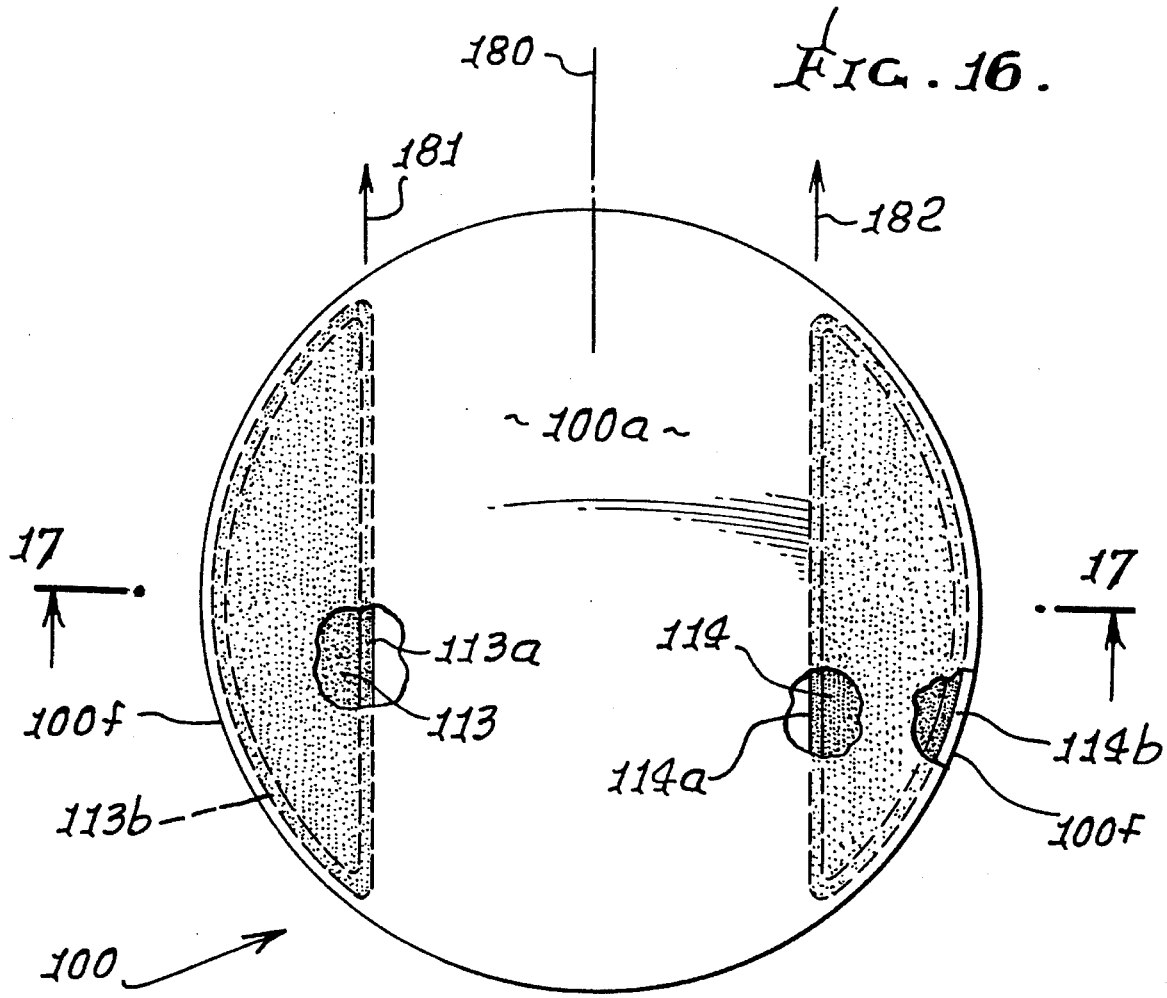
Figure 17:
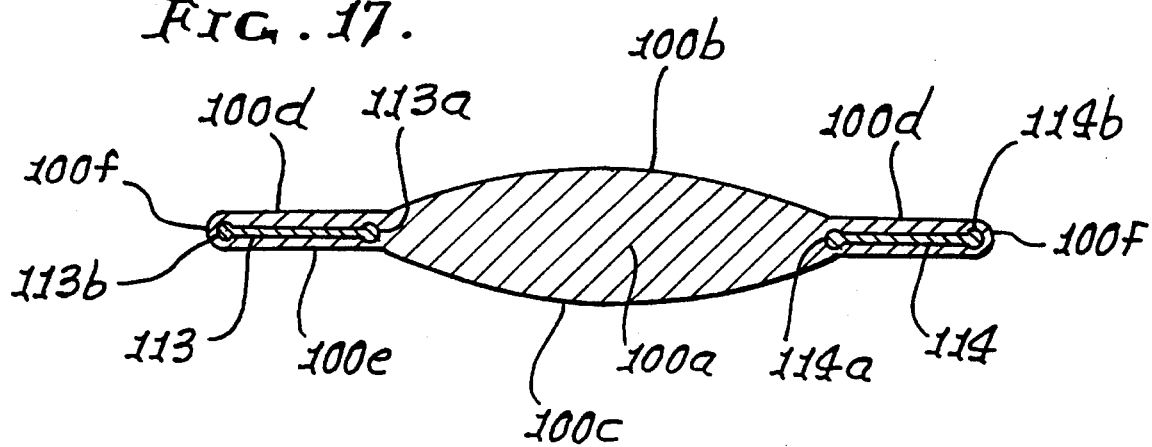
Figure 23:
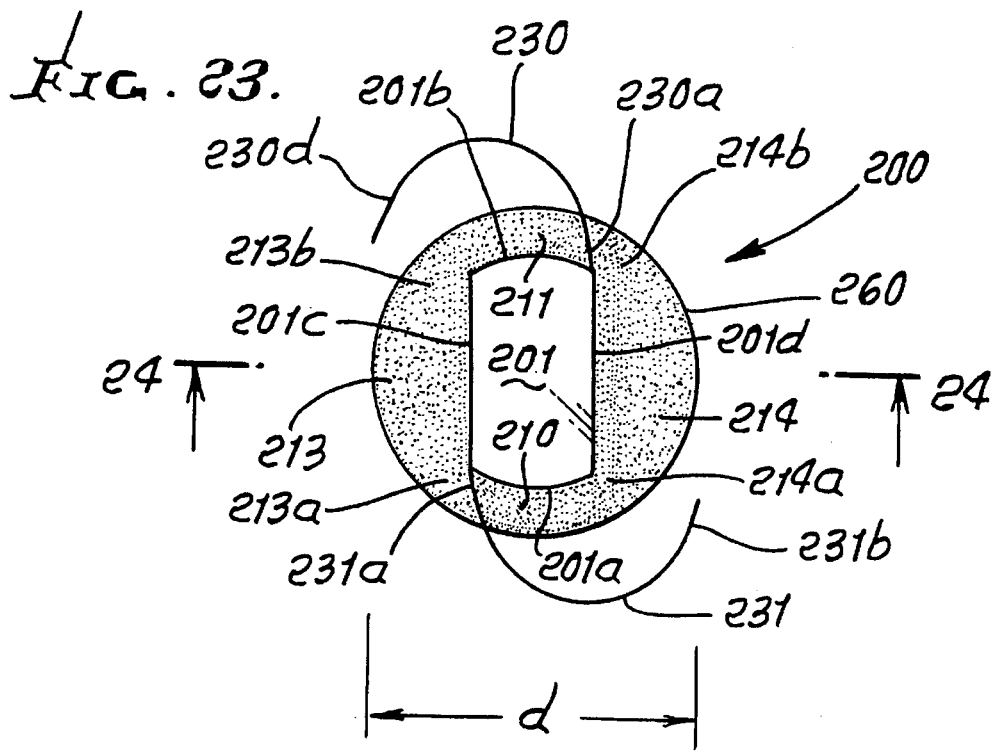
Figure 24:
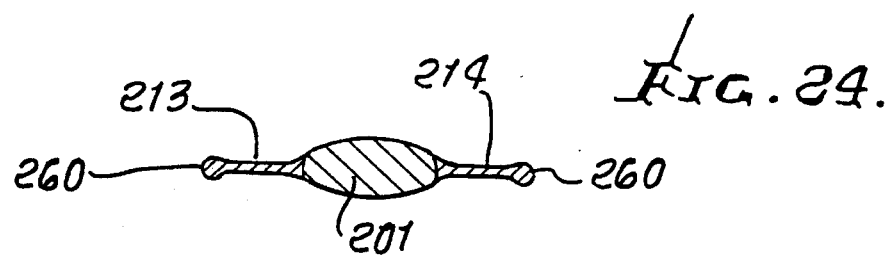
Figure 25:
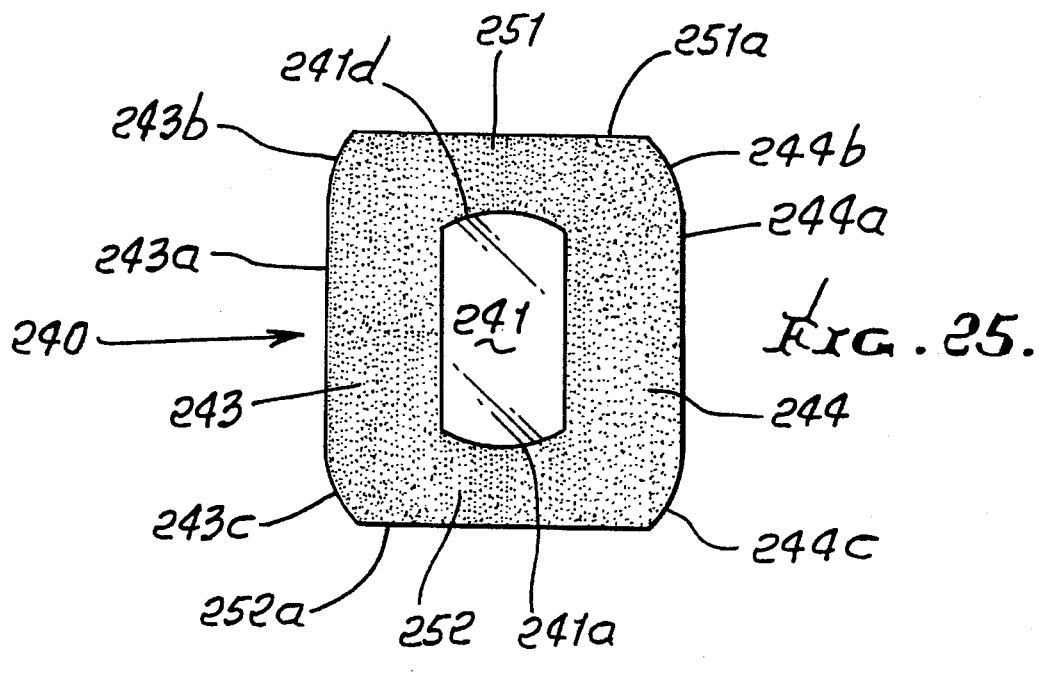
Figure 26:
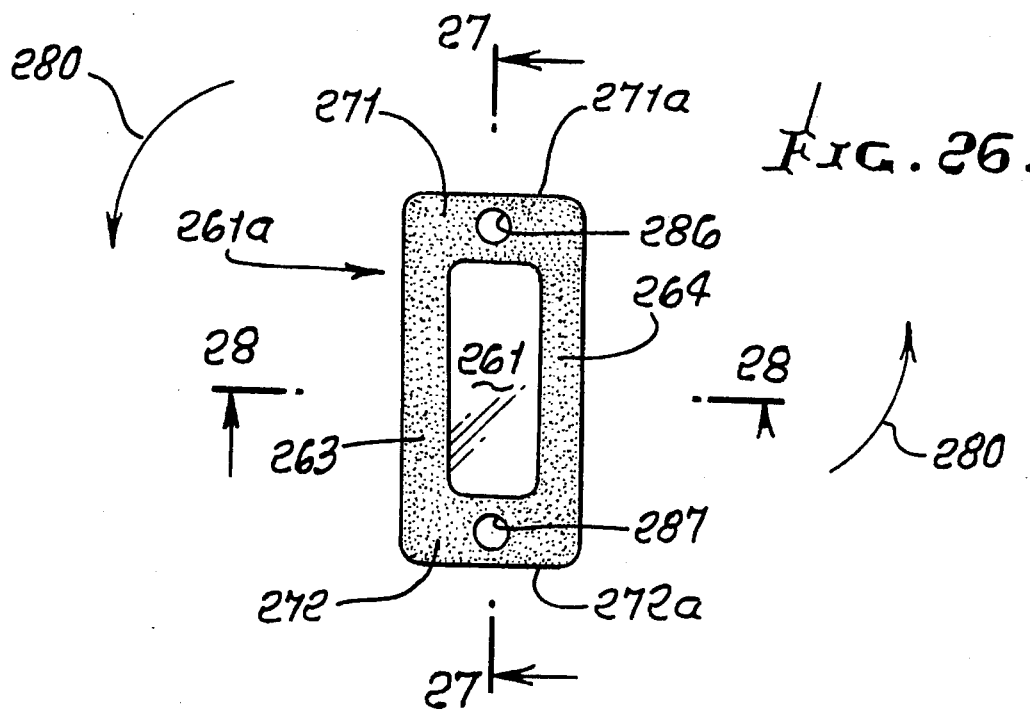

FIGS. 9 (a)–(g) are views showing progressive folding of the lens;

FIG. 10 is an edge view of a folded lens with folding forceps received in pockets formed by light blocking peripheral segments of reduced "de-bulked" thickness;

FIG. 11 is an enlarged view showing forceps blades holding a lens in folded condition;

FIG. 12 shows the FIG. 11 forceps blades in released condition;

FIGS. 13 and 14 show folded lens insertion into the eye;

FIG. 15 shows the released lens and light blocking segments in the eye;

FIG. 16 is a frontal view of a further modified plastic lens;

FIG. 17 is a section taken on lines 17—17 of FIG. 16;

FIG. 18 is a frontal view of a lens as in FIGS. 16 and 17, with attached solid haptics anchored to the lens;

FIG. 19 is an enlarged section taken on lines 19—19 of FIG. 18;

FIG. 20 is an enlarged section taken on lines 20—20 of FIG. 18;

FIG. 21 is an enlarged section taken on lines 21—21 of FIG. 18;

FIG. 22 is a frontal view of a lens as in FIGS. 16 and 17, but with spiral haptics anchored to the lens;

FIG. 23 is a view like FIG. 1 showing light-blocking structure surrounding the intermediate light-passing portion of the lens;

FIG. 24 is a section taken on lines 24—24 of FIG. 23;

FIG. 25 is a view of another modified lens, of larger dimension, with light-blocking structure surrounding the light passing intermediate portion;

FIG. 26 is a view like FIG. 23 showing a modification; and

Figure 27:
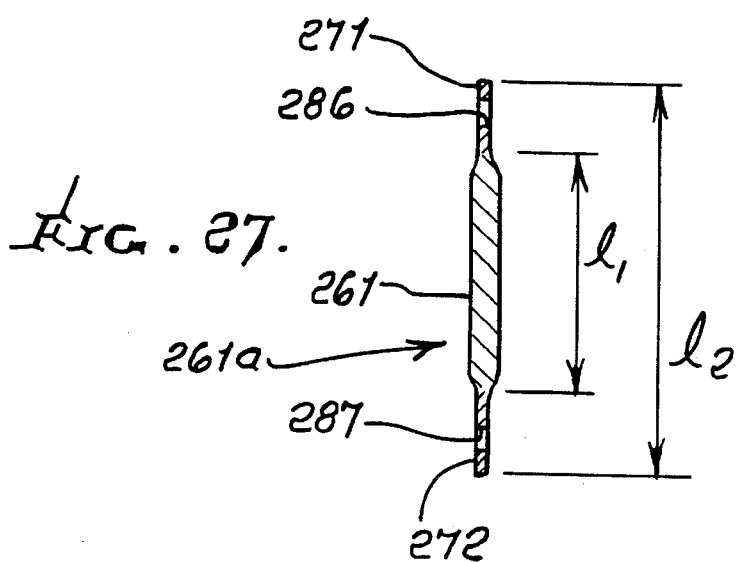
Figure 28:
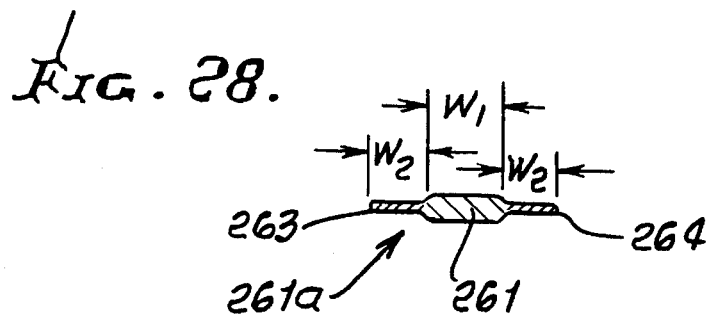

FIGS. 27 and 28 are sections taken on lines 27—27 and 28—28 of FIG. 26.

DETAILED DESCRIPTION

Figure 2:
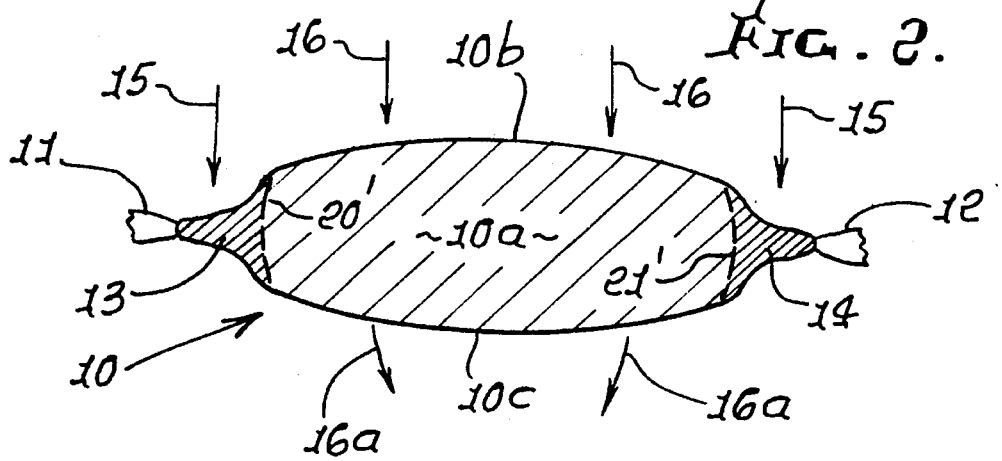
FIG. 2 is an enlarged section taken on lines 2—2 of FIG. 1.

In FIGS. 1 and 2, a plastic lens 10 is shown, sized for resiliently yieldable folding and insertion into the eye lens zone from which a natural but cataractous lens has been removed. One highly advantageous technique for such insertion is disclosed in U.S. Pat. No. 4,813,957, other techniques being usable. The bead-like lens, which may consist of silicon or equivalent material, has a light passing intermediate zone 10a between outwardly convex lens surfaces 10b and 10c. Attached to the lens generally circular periphery are two oppositely extending, solid haptics 11 and 12. Loop-type haptics may alternatively be employed. See the publication entitled "Simultaneously Intracapsular Implantation of Haptics and Optic Segment Using Cross-Action Folding Forceps", by Henry H. McDonald, M.D.

In accordance with one aspect of the invention, the lens also has two opposed peripheral segments 13 and 14, which are characterized as light blocking. They may be internally darkened, or cloudy, or occluded, or the surfaces of the segments may be treated so as to be irregular, or occluded, or darkened, to achieve light blocking effect. See light rays 15 in FIG. 2, blocked by 13 and 14; whereas, light rays 16 incident on the lens light passing and refracting intermediate portion 10a are not blocked, and pass from the lens at 16a. Further, the segments 13 and 14 have substantially reduced thickness (de-bulking) over their major extents, relative to the thickness of 10a over its major extent. Note also that the two segments typically have substantially equal size and shape, and they extend adjacent the intermediate optics portion 10a along substantially linear and parallel borders 20 and 21, as seen in FIG. 1. Such borders appear as planes 20' and 21' in FIG. 2. Also, the segments have generally convex outer edges 13a and 14a. Typical dimensions are as follows:

| d | 6 mm |
|---|------|
| e | 3 to 4 mm | where "d" is the diameter of the intermediate portion 10a, and "e" is the spacing between the segments, as seen in FIG. 1.

As also seen in FIG. 1, the lens has an optical axis 23; and there is a flat plane 24 containing that axis 23 that bisects both of the segments. That plane extends generally normal to the parallel, linear borders 20 and 21. Plane 24 also bisects the lens intermediate portion 10a. Each of the segments 13 and 14 has thickness which tapers or reduces directionally away from the intermediate portion 10a, as is seen in FIG. 2. Thus, the segments are de-bulked relative to intermediate portion 10a.

The haptics 11 and 12 are in the form of flat, foldable and flexible plastic tabs that extend directionally longitudinally oppositely (see arrows 25 and 26 in FIG. 1), whereby each segment 13 and 14 is elongated in skewed relation to the longitudinal direction of tab elongation. As will appear, these relationships facilitate superposition of the reduced thickness segments 13 and 14 during lens and tab folding, to minimize the overall width of the folded assembly for insertion through an incision in the corneo-scleral limbus. Also, as is clear from FIG. 2, the haptics have secure attachment to the lens at lens peripheral regions 70 and 71, offset from the thin segments 13 and 14 which offer less secure attachment of the haptics to the lens.

The lens also defines a fold axis 30 that bisects the intermediate optical portion 10a. See FIGS. 1, 3, 4, 5, and 6, the axis 30 passing through axis 23. Segments 13 and 14 are elongated in generally parallel relation to that fold axis 30, which extends crosswise of the longitudinal axis 34 of haptics elongation, at an acute angle, as seen in FIG. 3. Axis 34 also passes through axis 23.

FIGS. 5 and 6 show the resiliently foldable lens as having been folded along axis 30 to bring the de-bulked two segments 13 and 14 into superposition, i.e., maintains the segments in parallel, closely spaced relation. De-bulking of the lens segments 13 and 14 accordingly allows for forceps gripping of the lens at pockets formed by the outwardly facing tapered surfaces 13a and 14a of the segments, as seen in FIG. 10, significantly enhancing grippability of the folded lens by the forceps, and resultant assurance against forceps displacement relative to the lens as during folding, maneuvered insertion of the lens and haptics through a narrow width wound (for example about 3 mm) in the eye, as referred to, rotation of the folded lens in the eye to position the haptics, and during lens release to control said release and prevent lens "explosive" unfolding. See the forceps blades 40 and 41 in FIG. 10, received in the pockets shown.

Cross-over-type forceps may be employed for lens insertion in the eye "bag", as described in U.S. Pat. No. 4,813,957. FIGS. 11 and 12 show another type forceps 42 holding a lens 10, FIG. 12 showing the forceps controllably expanded to release the lens. FIG. 7 shows the use of cross-over forceps 44 (see cross-over point 45), with blades 40 and 41 extending in parallel relation, and placed adjacent segments 13 and 14. Blade arm of a holding forceps 46 projects oppositely as shown, as along the fold axis 30, to hold or position the lens 10 during folding. The forceps blades 40 and 41 may be pressed downwardly to fold the lens about axis 30. See FIG. 9, steps (c) through (g), showing progressive lens folding, as blades 40 and 41 are pressed down relative to blade 46. Blades 40 and 41 remain in the pockets formed by segment surfaces 13a and 14a (see FIG. 10) during such folding, the blades also being closed partially together during lens folding. Blade 46a is axially withdrawn as at or near step 9(f).

FIG. 9(a) shows a wound or incision 50 in the eye, and FIG. 9(b) shows a lens 10a, of FIGS. 1 and 2 type, haptics not being shown.

FIGS. 13 and 14 show insertion of the folded lens and haptics into an eye lens zone, via the narrow wound, and via the opening 50 of the anterior capsulatory 50. In FIG. 14, the folded lens and haptics are inserted more deeply than in FIG. 13, and the corner 11e of the forward haptic 11 becomes folded back, as shown.

FIG. 15 shows the unfolded lens and haptics in the eye 60. Segments 13 and 14 are positioned (by lens rotation) to extend generally horizontally, above and below the lens intermediate portion 10a; i.e., the portion 10a is elongated left and right to pass maximum left and right light through the lens to the eye retina, i.e., the effective width of the lens is not reduced, so as not to inhibit left and right vision. The occluded de-bulked segments 13 and 14 block light passage (light that would otherwise be distorted due to thinning or debulking at 13 and 14); but any inhibition of up-down vision is of lesser importance and such up-down vision is normally inhibited anyway by squinting of eyelids. The normal pupil appears at 61, and the expanded pupil at 61a.

Looping haptics may be employed in place of the tab-like haptics described.

In FIG. 10, note that the total thickness of the superposed two blades and two segments is substantially the same or less than the total thickness of the two halves of the folded intermediate optical portion of the lens.

In FIGS. 16 and 17, the bead-like silicon lens 100 is like lens 10 described above and is foldable at axis 180 into two halves. It has a light passing intermediate zone 100a between outwardly convex lens surfaces 100b and 100c.

The lens also has two opposed peripheral segments 113 and 114 characterized as light blocking. The segments are anchored to the lens intermediate portion, and anchoring means may take one or both of two forms, as shown.

In FIG. 17, the segments comprise thin webs embedded or encapsulated in lens plastic material, to anchor them to the lens intermediate portion, in the positions shown. See de-bulked lens material films 100d and 100e covering the opposite sides of the web-like segments and joined at 100f at the curved outer peripheries of the segments for further anchoring the segments. Also, and as another means of anchoring the segments, flexible, wire-like strands 113a and 114a are molded integrally with the segments, at their inner edges, and extend in parallel linear directions 180 and 181, along opposite borders of the lens intermediate portion 100a, and at the inner peripheries of the web-like segments as shown. Each such anchoring means has thickness substantially less than thickness of the main extent of the lens intermediate portion.

The foldable strands 113b and 114b may be integrally molded with the segments and have diameters larger than the thickness of the main extents of the segments.

The anchoring means may also extend along the outer peripheries of the segments. See reinforcement strands 113b and 114b, which extend arcuately near the outer peripheries 110f. Strands 113b and 114b, as well as reinforcement strands 113a and 114b, may be integrally molded with thin segments 113 and 114, as from plastic material, and the latter may be colored so as to be opaque, i.e., blocking to light transmission. See for example, silicone polymer lens material and polimide haptic material supplied by Stair Surgical, Monrovia, Calif. The segments and strands are flexible and foldable. Segments 113 and 114, together with the lens material layers 110d and 110e, have substantially reduced thickness (de-bulking) over their major extents, relative to the thickness of 110a over its major extent, and may have dimensions about the same as segments 13 and 14 described above.

Referring now to FIG. 18, the construction is the same as in FIGS. 16 and 17 but haptics and additional reinforcement strands are provided. Note strands 120a and 121a extending along the curved peripheral sections of the lens intermediate region 110a and incorporated in the lens material. Such strands may be formed as continuations of strands 114a, and may intersect strands 13a at their ends.

In FIGS. 18–21, like haptics 111 and 112 are in the form of flat, foldable and flexible plastic tube, like those described above at 11 and 12. Lengthwise folding of the lens along "bisecting" axis 180 also results in "bisecting" folding of the two haptics. Folding can also be carried out as in FIGS. 1–15, or along an axis 181 extending proximate ends of the segments, as seen in FIG. 16. The reinforcement strands 120a and 121a also act to assist anchoring of the two haptics 111 and 112 to the lens intermediate portion 100a. See FIG. 21. Reinforcement strands may also be molded into (encapsulated in) the haptics, near their outer edges, as indicated at 130a–130c, and 131a–131c. The haptics may consist of polimide; whereas, the strands 130 and 131 may consist of the same material as segments 113 and 114, or associated strands as described. Corner portions of the haptics may define one or more through openings, seen at 132 and 133, to allow growth of eye tissue through such openings, to assist in positioning the haptics in the eye, as described above in FIG. 15. Segments 113 and 114 may be obliquely angled relative to axis 180, as in FIG. 1.

FIG. 22 shows a lens like that of FIGS. 16 and 17 but having two lens positioning haptics 150 and 151 comprising narrow (plastic, such as polimide) fingers with inner end portions 150a and 151a anchored by the anchor strands 113b and 114b. Such anchoring may be by suitable attachment to 113b and 114b near cusps 113a' and 114b'. Portions 150a extend sidewise generally parallel to 113b and 114b. Outer end portions of the two haptics curl at 150b and 151b, as conventional. They may consist of molded plastic material. Their positioning enables folding overlay of the haptics, for implantation, if the fold is along axis 300.

Referring back to FIG. 18, the strands 113a, 113b, 114a, 114b, 130a –c, and 131a –c may be preliminarily formed or molded as a "skeleton", to provide reinforcement when the silicon lens is molded to integrate and encapsulate the "skeleton" or framework, with the haptics forming the complete article. Strands 120a and 121a may be included in the skeleton.

Referring now to FIGS. 23 and 24, a modified plastic lens 200 is shown. The bead-like intermediate portion 201 may consist of silicone or equivalent material. The lens also has a peripheral portion or portions bounding the intermediate portion and characterized as flexible and substantially light blocking; and in this regard, such portion or portions may be light occluding. They may be internally darkened or cloudy or occluded, or the surfaces of such portion or portions may be treated so as to be irregular or occulated or darkened to achieve a light-blocking effect. Darkening may occur as during molding.

As shown, the portions 213 and 214 at opposite elongated sides of the intermediate portion 201 correspond to portions or segments 13 and 14 in FIG. 1; however, they are larger in area than such portions 13 and 14. In this regard, the endwise extents 213a and 214a of the portions 213 and 214 project beyond the curved end 201a of the intermediate portion 201; and an additional light-blocking portion 210 extends adjacent 201a and between the extents 213a and 214a so as to completely bound the edge 201a of the light blocking intermediate portion.

Likewise, the endwise extents 213b and 214b of portions 213 and 214 project beyond the curved edge 201b of the intermediate lens portion 201; and an additional light-blocking portion 211 extends adjacent edge 201b and between the extents 213b and 214b to completely bound the opposite end of the intermediate portion 201. Thus, the intermediate portion is completely bounded, or may be substantially completely bounded, by light-blocking plastic 213, 214, 210, and 211; and the latter portions may be molded as a single portion and using the same plastic material, as for example silicon; and it may be de-bulked, i.e., have reduced thickness relative to the intermediate portion 210, all the way around the latter. See for example FIG. 24 showing such reduced thickness at 213 and 214, portions 210 and 211 having similarly reduced thickness.

The peripheral edge or edges of portions 213, 214, 210, and 211 may be reinforced and consist of a plastic or synthetic resinous material different from the silicone of the intermediate portions 213,214,210,211, and 201. See for example boundary edge 260. One example of such material is the polimide referred to above. It will be understood that the molding process results in integral attachment or formation of 201 to 213,214,210, and 211, as well as edge or edge strip 260.

Elongated edges of the intermediate portion appear at 201c and 201d, these being typically parallel and merging with rounded edges 201a and 201b.

The lens structure, as shown in FIG. 23, may have an overall cross dimension "d", which is about 8–9 mm and may be inserted edgewise into the eye through an appropriate slit cut therein. Filament-type haptics 230 and 231 may be formed with or attached to the lens at their root ends 230a and 231a shown as extending adjacent to or molded integrally with the de-bulked portions 211 and 210, and stemming from edges 201c and 201d. The haptic filaments are also curved outwardly and back toward the lens at regions 230d and 2310b.

Referring now to FIG. 25, the modified lens 240 incorporates an intermediate, thicker, light-passing portion 241, corresponding generally to portion 201 in FIG. 23. Side portions or segments 243 and 244 correspond generally to side portions 213 and 214 in FIG. 23; and bounding end portions 251 and 252 adjacent the ends 241d and 241a of portion 241 extend in bounding relation to the ends of the lens portion 241, whereby, that intermediate portion 241 is completely or substantially bounded by light blocking (as for example occluding), de-bulked or thinned lens structure, the latter for example consisting essentially of silicone, as referred to earlier; and, the intermediate portion 241 also consists essentially of silicon. A single integral structure can thereby be produced in a very easy manner, and may be foldable or non-foldable.

The bounding structure 243, 244, 251, and 252 may have a generally rectangular outline, with edges 243a and 244a, which are parallel, and edges 251a and 252a, which are generally parallel. Corners 243b and c, and corners 244b and c are arcuate, as shown.

The bounding structure proximate edges 251a and 252a may act as or provide tabular haptics, i.e., locating means in the eye. The overall cross dimension "e" of the FIG. 25 lens may be 8 mm or 9 mm, and this "enlarged" structure may be suitably inserted into the eye via an appropriate slit cut therein.

In FIGS. 26–28, the modified lens unit 260 is like that of FIG. 25, with intermediate, thicker, light-passing portion 261, side portions or segments 263 and 64 (corresponding to 243 and 244) and bounding end or side portions or segments 271 and 272 (corresponding to 51 and 252). Portion 261 is completely bounded by light-blocking or occluding portions 263, 264, 271, and 72, the latter being debulked, i.e., much thinner than light-passing portion 261. All such portions consist of molded silicon. Surfaces of 263, 264, 271, and 272 may be rough, to be light occluding.

The width $w_1$ of portion 261 may, for example, be 3 mm; and the width $w_2$ of each of 263 and 264 may be ½ mm. Therefore, the total width of the lens unit 260 is 6 mm. The overall length "$l_2$" of the unit may be about 10 mm; and the length "$l_1$" of light-passing portion 261 may be about 6 mm. Therefore, unit 261a is elongated, as shown in the vertical or length direction, as oriented during insertion. After insertion, the unit is rotated about 90° in the direction of arrows 280, so that the $l_1$ dimension then extends horizontally in the eye. Boundary structure proximate edges 271a and 272a acts as or provides tabular haptics.

Through holes 286 and 287 in portions 271 and 272 are adapted to receive tissue in the eye, for assisting in locating the unit in the eye.

I claim:

1. A plastic lens insertible into the eye lens zone from which a natural lens has been removed, comprising
   a) the plastic lens having a light passing intermediate optical portion,
   b) the lens also having a peripheral portion or portions bounding said intermediate optical portion and characterized as substantially light blocking, and including haptic means extending integrally with said peripheral portion or portions,
   c) said lens having overall length and overall width, said length substantially exceeding said width,
   d) said optical portion and said peripheral portion or portions having one-piece molded construction, e) and wherein said peripheral portion or portions extend completely about said intermediate optical portion, and have reduced thickness relative to an outermost extent of said intermediate optical portion, and at locations directly bounding said intermediate optical portion outermost extent, said reduced thickness being tapered away from an outermost extent of said intermediate optical portion of the lens, f) and wherein said intermediate optical portion is substantially rectangular in outline.

2. The lens of claim 1 wherein said haptic means includes two haptics connected to said light-blocking peripheral portion or portions.

3. The lens of claim 1 wherein said peripheral portion or portions have substantially reduced thickness relative to the thickness or thicknesses of said intermediate optical portion.

4. The lens of claim 1 wherein said intermediate portion is light transparent, and said peripheral portion or portions are opaque.

5. The lens of claim 1 wherein said haptic means includes two haptics that comprise flat tabs projecting oppositely.

6. The lens of claim 1 wherein said intermediate portion consists essentially of silicone, and said peripheral portion or portions consist essentially of a synthetic resin.

7. The lens of claim 1 wherein said intermediate portion has two laterally spaced parallel edges which are elongated relative to the lateral spacing of said edges.

8. The lens of claim 1 wherein said peripheral portion or portions define a substantially rectangular outer border.

9. The lens of claim 8 wherein said outer border has arcuate corners.

10. The lens of claim 8 wherein said rectangular border has overall width and overall length, said length substantially exceeding said width.

11. The lens of claim 10 wherein there are through openings in certain of said peripheral portion or portions.

* * * * *